United States Patent [19]

Motoki et al.

[11] 4,054,735

[45] Oct. 18, 1977

[54] STABILIZED N$^2$,2-O-DIBUTYRYLGUANOSINE-3,5-CYCLIC PHOSPHATE AND SALTS THEREOF

[75] Inventors: Goro Motoki; Kazuo Uchida; Hiroshi Yoshino, all of Choshi, Japan

[73] Assignee: Yamasa Shoyu Kabushiki Kaisha, Japan

[21] Appl. No.: 573,157

[22] Filed: Apr. 30, 1975

[30] Foreign Application Priority Data

May 14, 1974  Japan ................................ 49-52866

[51] Int. Cl.$^2$ .......................................... C07H 19/20
[52] U.S. Cl. ...................................... 536/28; 536/27; 536/22
[58] Field of Search ................... 260/211.5 R; 536/28

[56] References Cited

U.S. PATENT DOCUMENTS

| | | | |
|---|---|---|---|
| 3,190,877 | 6/1965 | Ishibashi et al. | 260/211.5 R |
| 3,712,885 | 1/1973 | Weimann et al. | 260/211.5 R |
| 3,852,267 | 12/1974 | Meyer, Jr. et al. | 260/211.5 R |
| 3,856,776 | 12/1974 | Cehovic et al. | 260/211.5 R |

OTHER PUBLICATIONS

Meyer, Jr. et al. "Tetrahedron Letters" No. 4, pp. 269-272, 1973, Pergamon Press, New York, N. Y.

*Primary Examiner*—Johnnie R. Brown
*Attorney, Agent, or Firm*—Wenderoth, Lind & Ponack

[57] ABSTRACT

N$^2$,2'-O-dibutyrylguanosine-3',5'-cyclic phosphate or a salt thereof is stabilized by adjusting the moisture content thereof to 3 percent or less by weight.

4 Claims, 4 Drawing Figures

STABILIZED N²,2-O-DIBUTYRYLGUANOSINE-3,5-CYCLIC PHOSPHATE AND SALTS THEREOF

BACKGROUND OF THE INVENTION

This invention relates generally to dibutyrylguanosine cyclic phosphate compounds which have been stabilized with respect to decomposition. More particularly, the invention relates to stabilization against decomposition of $N^2,2'$-O-dibutyrylguanosine-3',5'-cyclic phosphate and salts thereof (hereinafter referred to by the abbreviation DCc - GMP).

In recent years, DBc, - GMP together with guanosine-3',5'-cyclic phosphate and salts thereof have attracted attention as being very useful substances in pharmacology, and uses thereof are being developed as pharmaceutical and medical goods and as reagents for use in biochemical research. Among the numerous advantageous features of DBc - GMP, their high solubility in a large variety of solvents beginning with water and their excellent permeability through cell membranes have been cited.

However, DBc - GMP are unstable at room temperature and even when they are preserved at low temperatures, their rates of decomposition increase further particularly under acidic or alkaline conditions. Under alkaline conditions, DBc - GMP undergo hydrolysis into $N^2$-monobutyrylguanosine-3',5'-cyclic phosphate and salts thereof (hereinafter referred to by the abbreviation $N^2$-MBc-GMP). Under acidic conditions, on the other hand, DBc - GMP undergo hydrolysis into 2'-O-monobutyrylguanosine-3',5'-cyclic phosphate and salts thereof (hereinafter referred to by the abbreviation 2-O-MBc-GMP). The rates of these hydrolyses increase with the degrees of alkalinity and acidity.

Since DBc - GMP have an unstable property of this nature, they not only require extreme care during the production process with respect to conditions such as temperature and pH level but require particular care also in the preservation of the product. For example, even in the case where DBc - GMP are preserved as solid preparations at a low temperature, it has heretofore been difficult to preserve them in a stable state, and it has been necessary to devise special methods of transportation during handling procedures such as transportation. Because of this unstable character of DBc - GMP, their handling has been difficult, which has been a great obstruction to their development in spite of their usefulness.

As a result of our various researches directed toward overcoming these difficulties and obstruction, we have discovered that when the moisture (water) content of a DBc - GMP in solid state is held at or below 3 percent (all percentages herein being by weight), preferably below 2.5 percent, the DBc - GMP exhibits a high stability, and this discovery is a basis of this invention as described more specifically hereinafter.

SUMMARY OF THE INVENTION

It is an object of this invention to provide DBc - GMP in solid state which are stabilized by being so prepared that their water content does not exceed 3 percent.

According to this invention in one aspect thereof, there is provided a stabilized dibutyrylguanosine cyclic phosphate compound selected from the group consisting of $N^2,2'$-O-dibutyrylguanosine-3',5'-cyclic phosphate and salts thereof and having a moisture content of not more than 3 percent by weight.

According to this invention in another aspect thereof, briefly summarized, there is provided a method for producing a stabilized dibutyrylguanosine cyclic phosphate compound selected from the group consisting of

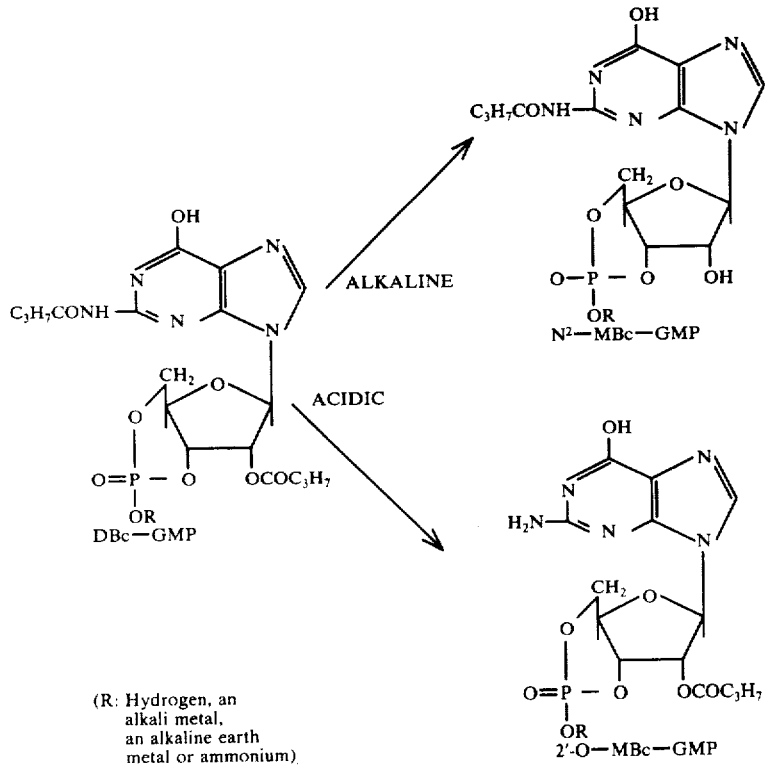

(R: Hydrogen, an alkali metal, an alkaline earth metal or ammonium)

$N^2,2'$-O-dibutyrylguanosine-3',5'-cyclic phosphate and salts thereof and having a moisture content of not more than 3 percent by weight, which method comprises subjecting a dibutyrylguanosine cyclic phosphate compound selected from the group consisting of $N^2,2'$-O-dibutyrylguanosine-3',5'-cyclic phosphate and salts thereof and having a moisture content of more than 3 percent by weight to desiccation for a time sufficient to reduce the moisture content to not more than 3 percent by weight.

The nature, principle, utility, and further features of the invention will be apparent from the following detailed description beginning with a consideration of general features of the invention and concluding with specific examples of practice illustrating preferred embodiments of the invention when read in conjunction with the accompanying drawings.

DETAILED DESCRIPTION

In this invention, the term DBc - GMP is intended to include amorphous powder and crystalline solid preparations of $N^2,2'$-O-dibutyrylguanosine-3',5'-cyclic phosphate and salts thereof, examples of these salts being alkali metal salts such as a sodium salt and a potassium salt; alkaline earth metal salts such as a calcium salt, a barium salt, and a magnesium salt; and an ammonium salt.

Figure 1:
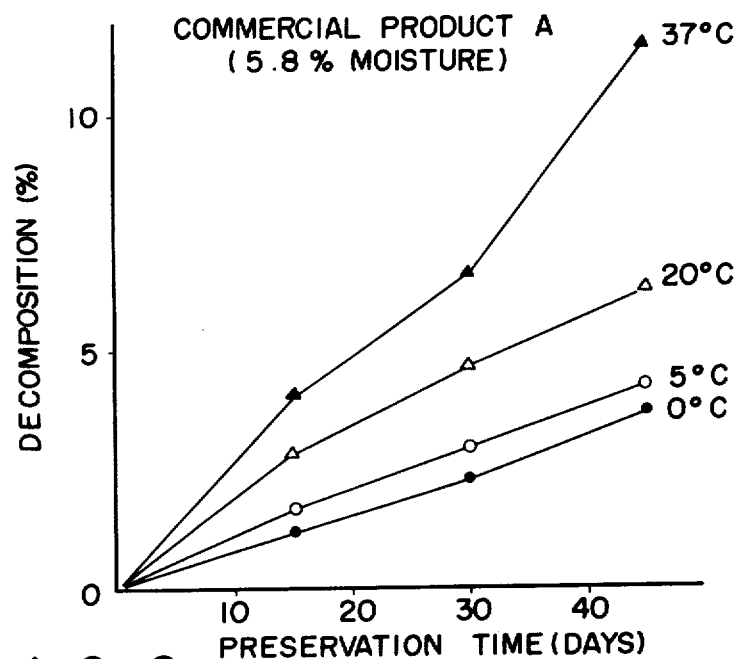
FIGS. 1 and 2 are graphical representations respectively indicating, in terms of relationships between preservation time (in days) and decomposition (in percent) at various temperatures, the stabilities of two DBc - GMP preparations sold on the market.
Figure 2:
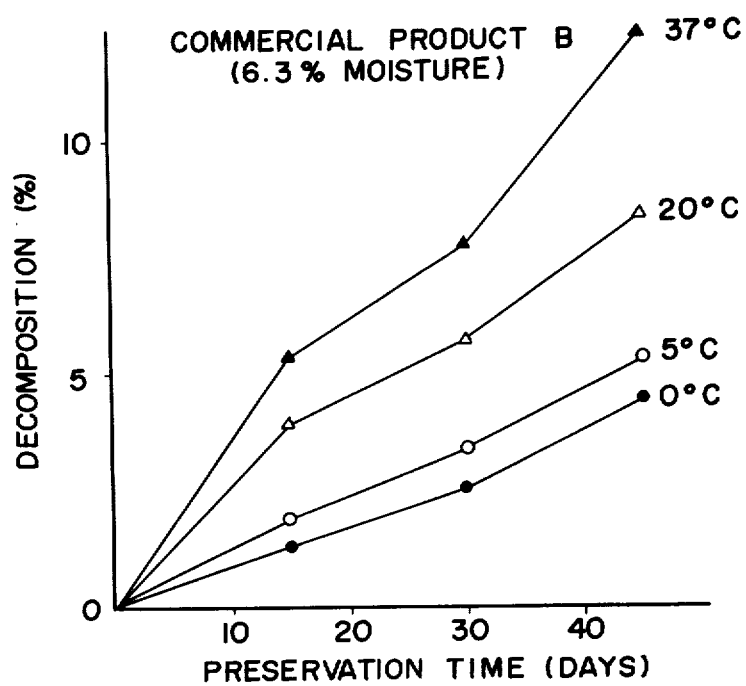

In known DBc - GMP preparations, for example, commercial products (sodium salt) A and B with moisture contents of 5.8 and 6.3 percent, respectively, decomposition of the DBc - GMP in each case advances with elapse of preservation time and becomes even higher as the preservation temperature increase as indicated in FIGS. 1 and 2. It is apparent from this that these DBc - GMP are extremely unstable.

As a result of our various studies made with the object of stabilizing DBc - GMP, we have discovered that a close relationship exists between the moisture content and stability of a DBc - GMP. More specifically, the stability of a DBc - GMP in a solid state varies remarkably at a critical boundary in the vicinity of a moisture content of the DBc - GMP of 3 percent. In the case of a moisture content of 4 percent or more, stability is abruptly lost as the moisture content increases, and the DBc - GMP exhibits a tendency to be hydrolized into $N^2$-MBc-gMP or 2'-O-MBc-GMP.

We have found the surprising fact that, in spite of this remarkable instability at a moisture content of 4 percent or more, the DBc - GMP exhibits a high stability whereby it can be preserved stably for at least 60 days even at a preservation temperature of 37° C when the moisture content is reduced to 3 percent or less.

Figure 3:
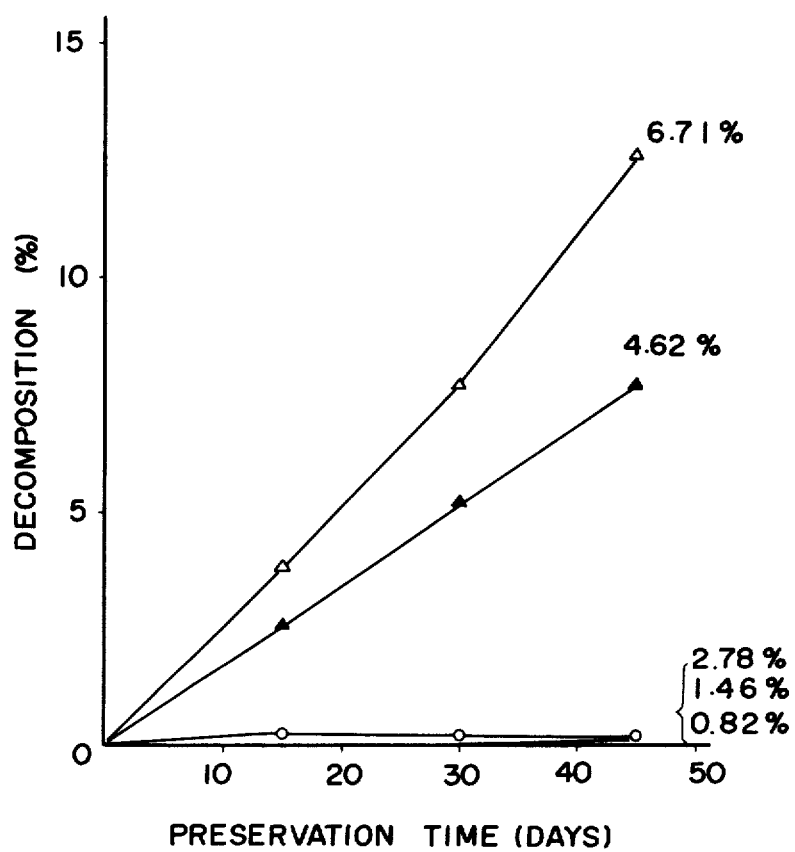
FIG. 3 is a similar graph showing results of experiments and indicating the effect of moisture content on the stability of a DBc - GMP preparation.

This phenomenon is indicated in FIG. 3 which shows the results of experiments carried out to compare the stabilities of DBc - GMP with various moisture contents preserved under the severe preservation condition of a temperature of 37' C. Details are set forth in Example 6 to follow. It is apparent from these results that DBc - GMP preparations with moisture contents of 3 percent or less are preserved with complete stability, and the effectiveness of this invention is fully demonstrated.

Figure 4:
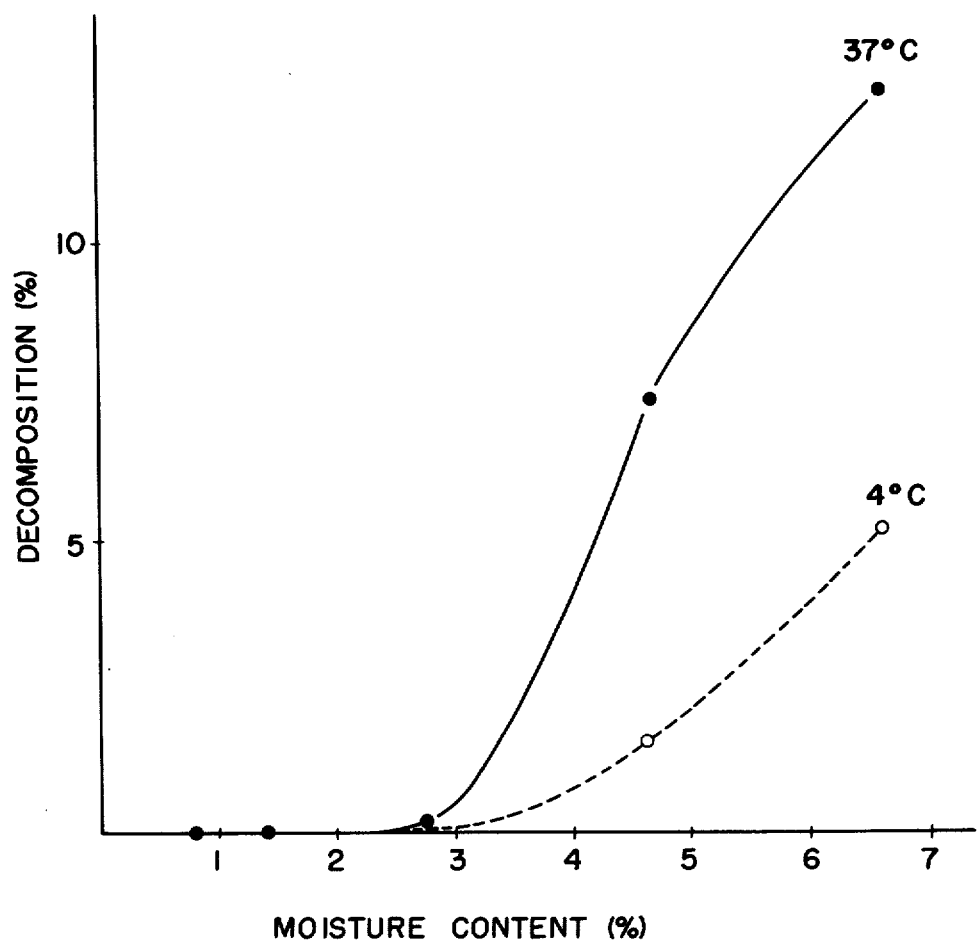
FIG. 4 is a graph indicating the variation of stability with moisture content of DBc - GMP Na stored for 45 days at two different temperatures.

The stabilities of DBc - GMP·Na at various moisture contents when stored for 45 days at two different temperatures are indicated in FIG. 4. It is apparent from these results that an abrupt variation in the stability occurs in the vicinity of 3-percent moisture content as a critical boundary, not only in the case of a perservation temperature of 4° C but even under the severe condition of a preservation temperature of 37° C. Thus, it can be concluded from these results that the moisture content of 3 percent is critical for the stabilities of DBc - GMP and their salts.

Now, except for the condition that the moisture content is 3 percent or less and, accordingly, the result that practically no decomposition is observable, a stabilized DBc - GMP preparation provided in accordance with this invention has chemical and physical properties which do not differ essentially from those of known or conventional DBc - GMP preparations. Therefore, specific information on the chemical and physical properties of a DBc - GMP preparation according to this invention can be obtained from various pertinent chemical dictionaries, handbooks, and textbooks.

For adjusting the moisture content of a DBc - GMP so that it will not exceed 3 percent in the practice of this invention, various drying (desiccating) methods can be applied. Some examples of these methods are the desiccation under reduced pressure or in vacuo, the desiccation the method over a desiccant such as a hygroscopic agent, the desiccation over a desiccant under reduced pressure or in a vacuo, the freeze-drying, the spray drying under reduced pressure or in vacuo and the azeotropic dehydration with an organic solvent. From these methods, one method or a combination of methods can be suitably selected.

In addition, any method whereby the DBc - GMP preparation can be dried under the condition that its temperature is maintained at room temperature or lower temperature can be effectively applied in the practice of this invention. Desiccation at an elevated temperature is not desirable since the DBc - GMP decomposes before its moisture content reaches 3 percent at which its stability increases. However, raising the temperature of the DBc - GMP after the moisture content has reached a value in the vicinity of 3 percent in the desiccating process step, and the DBc - GMP has become relatively stable is effective since the drying time can then be shortened.

A desiccant or a hygroscopic agent ordinarily used for desiccation or drying can be used in the practice of this invention. Examples of effective desiccants are phosphorus pentoxide, calcium chloride, silica gel, and concentrated sulfuric acid.

Irrespective of whether the prepared form of a DBc - GMP is an amorphous powder form or whether it is crystalline, a stable DBc - GMP can be obtained by adjusting its moisture content to 3 percent or less by the above described method.

In order to indicate more fully the nature and utility of this invention, the following specific examples of practice constituting preferred embodiments thereof are set forth, it being understood that these examples are presented as illustrative only and that they are not intended to limit the scope of the invention.

EXAMPLE 1

A DBc - GMP (sodium salt) of a moisture content of 5.98 percent obtained by freeze-drying was desiccated in vacuo for 5 hours at 25° C, under 1 mm. Hg, and in the presence of phosphorus pentoxide, whereupon the moisture content of the DBc - GMP became 0.91 percent. This DBc - GMP was placed in glass bottles, which were sealed and stored for 45 days respectively at 20° C and 37° C. The contents of the bottles were then analyzed, and as a result it was found that decomposition of the DBc - GMP during the storage period had not proceeded at all, whereby it could concluded that the DBc - GMP was fully stable.

EXAMPLE 2

The DBc - GMP of 0.91-percent moisture content of Example 1 was caused to absorb moisture in a vessel saturated with moisture at room temperature and three samples of the DBc - GMP were adjusted respectively to moisture contents of 1.52 percent, 2.86 percent, and 5.34 percent. Each of these samples were further divided into three samples which were stored for 45 days under the conditions specified in Example 1 respectively at 20° C, 37° C, and 50° C.

As a result, no decomposition whatsoever was observable in the samples of moisture contents of 1.52 percent and 2.86 percent which were stored at 20° C and 37° C, and only these sampls which had been stored at 50° C exhibited a very small increase of 2'-O-MBc-GMP, the DBc-GMP having been preserved very stably. The DBc-GMP sample ajusted to the moisture content of 5.34 percent exhibited a decomposition of 5.87 percent at the storage temperature of 20° C, 10.92 percent at 37° C, and 36.47 percent at 50° C, and 2'-O-MBc-GMP, N²-MBc-GMP, and c-GMP were detected in addition to the DBc - GMP.

EXAMPLE 3

A DBc - GMP (potassium salt) of a moisture content of 6.1 percent was desiccated for 4 hours at 24.5° C, over sulfuric anhydride under 1 mm. Hg, whereupon a DBc - GMP (potassium salt) preparation of a moisture content of 1.07 percent was obtained.

With samples of this preparation, preservation tests were carried out under the conditions specified in Example 1. As a result, no decomposition whatsoever was detected during the preservation period, whereby the stability of this preparation was indicated.

EXAMPLE 4

A DBc - GMP (acid) of a moisture content of 5.84 percent was dried under the conditions set forth in Example 1, whereupon a DBc - GMP (acid) preparation of a moisture content of 1.03 percent was obtained.

Preservation tests were carried out on samples of this preparation under the conditions set forth in Example 1. As a result, it was found that this preparation could be preserved stably except for detection of a very small quantity of 2'-O-MBc-GMP in the case of storage at 37° C.

As a comparison reference, the preparation of 5.84-percent moisture content prior to the above described desiccation was subjected to the same preservation test. As a result, it was found that 13.87 percent of the sample stored at 20° C and 21.46 percent of the sample stored at 37° C had decomposed into 2'-O-MBc - GMP and c - GMP.

EXAMPLE 5

A DBc - GMP (calcium salt) of a moisture content of 6.2 percent was desiccated in vacuo over silica gel for 4 hours at 25° C, under 1 mm. Hg., whereupon a DBc - GMP (calcium salt) preparation of a moisture content of 0.98 percent was obtained.

Preservation tests were carried out on samples of this preparation under the conditions specified in Example 1. As a result, no decomposition whatsoever was detected during the preservation period, whereby stability was indicated.

As a comparison reference, the preparation of 6.42-percent moisture content prior to the above described desiccation was subjected to the same preservation test. As a result, it was found that 11.92 percent of the sample stored at 20° C and 19.87 percent of the sample stored at 37° C had decomposed into 2'-O-MBc-GMP and c-GMP.

EXAMPLE 6

A DBc - GMP (sodium salt) of a moisture content of 5.85 percent obtained by freeze-drying of the wet salt was processed as set forth in Example 1, whereupon a DBc - GMP (sodium salt) preparation of a moisture content of 0.82 percent was obtained.

By further processing this preparation similarly as in Example 2, DBc - GMP (sodium salt) preparations respectively of moisture contents of 1.46, 2.78, 4.62, and 6.71 percent were prepared.

As a result of preservation tests on these preparations under the temperature conditions of 4° C and 37° C, decompositions as shown i Table 1 were measured.

Table 1.

| Temp.: | Decomposition (%) 4° C | | | 37° C | | |
|---|---|---|---|---|---|---|
| Storage: | 15 days | 30 days | 45 days | 15 days | 30 days | 45 days |
| Moisture content (%) | | | | | | |
| 0.82 | 0 | 0 | 0 | 0 | 0 | 0 |
| 1.46 | 0 | 0 | 0 | 0 | 0 | 0.05 |
| 2.78 | 0 | 0 | 0.04 | 0.11 | 0.20 | 0.28 |
| 4.62 | 0.47 | 0.92 | 1.60 | 2.48 | 5.16 | 7.46 |
| 6.71 | 1.29 | 3.14 | 5.11 | 3.88 | 7.64 | 12.65 |

These preservation test results at 37° C are indicated with respect to elapse of time in FIG. 3. The relationships between the moisture content and the stability of DBc - GMP (sodium salt) on the basis of results of storage for 45 days at 4° C and 37° C are indicated in FIG. 4.

METHOD OF MEASURING DECOMPOSITION

Each preserved DBc - GMP sample, 200 g, was subjected to paper chromatography (ascending method, developer solvent, isopropanol; 0.5 M ammonium acetae = 5 : 2, Toyo filter paper No. 53), and the spots respectively of DBc - GMP and MBc - GMP, c - GMP which are products of decomposition thereof were extracted with 5 ml. of water at from 0° to 5° C. The absorbance of the extract supernatant liquid at O.D. 260 was measured with a spectrophotometer (HITACHI-124), and the decomposition was determined from the following equation.

$$\text{Decomposition (\%)} = \frac{B + C}{A + B + C} \times 100,$$

where:
- A is the absorbance of DBc - GMP
- B is the absorbance of MBc - GMP
- C is the absorbance of c - GMP
- DBc - GMP : $N^2,2'$-O-dibutyrylguanosine-3',5'-cyclic phosphate, acid or salt
- MBc - GMP : $N^2$- or 2'-O-dibutyrylguanosine-3',5'-cyclic phosphate, acid or salt
- c - GMP : Guanosine-3',5'-cyclic phosphate, acid or salt

What is claimed is:

1. A method for producing a stabilized dibutyrylguanosine cyclic phosphate compound selected from the group consisting of $N^2,2'$-O-dibutyrylguanosine-3',5'-cyclic phosphate and salts thereof which has a moisture content of not more than 3 percent by weight, which method consists essentially of subjecting a dibutyrylguanosine cyclic phosphate compound selected from the group consisting of $N^2,2'$-O-dibutyrylguanosine-3',5'-cyclic phosphate and salts thereof selected from the group consisting of alkali metal salts, alkaline earth metal salts and ammonium salts, having a moisture content of more than 3 percent by weight to desiccation for a time sufficient to reduce the moisture content to not more than 3 percent by weight.

2. A method according to claim 1 in which the dessication is carried out under such conditions that the temperature of the dibutyrylguanosine phosphate compound is maintained at about room temperature or lower during the dessication thereof.

3. A method according to claim 2 wherein the moisture content is 0.91%.

4. A method according to claim 2 wherein the moisture content is 0.82%.